US011670415B2

(12) United States Patent
Yamamoto et al.

(10) Patent No.: US 11,670,415 B2
(45) Date of Patent: *Jun. 6, 2023

(54) DATA DRIVEN ANALYSIS, MODELING, AND SEMI-SUPERVISED MACHINE LEARNING FOR QUALITATIVE AND QUANTITATIVE DETERMINATIONS

(71) Applicant: Included Health, Inc., San Francisco, CA (US)

(72) Inventors: Seiji James Yamamoto, San Francisco, CA (US); Ranjit Chacko, San Francisco, CA (US)

(73) Assignee: INCLUDED HEALTH, INC., San Francisco, CA (US)

( * ) Notice: Subject to any disclaimer, the term of this patent is extended or adjusted under 35 U.S.C. 154(b) by 230 days.

This patent is subject to a terminal disclaimer.

(21) Appl. No.: 17/127,590

(22) Filed: Dec. 18, 2020

(65) Prior Publication Data

US 2021/0104316 A1 Apr. 8, 2021

Related U.S. Application Data

(63) Continuation of application No. 16/119,018, filed on Aug. 31, 2018, now Pat. No. 10,872,692, which is a
(Continued)

(51) Int. Cl.
*G16H 40/20* (2018.01)
*G16H 50/20* (2018.01)
(Continued)

(52) U.S. Cl.
CPC ........... *G16H 40/20* (2018.01); *G06F 16/285* (2019.01); *G06F 16/9024* (2019.01);
(Continued)

(58) Field of Classification Search
CPC ...... G16H 40/20; G16H 50/20; G06F 16/285; G06F 16/9024; G06F 16/355; G16Z 99/00; G06Q 10/10; G06Q 50/22
(Continued)

(56) References Cited

U.S. PATENT DOCUMENTS

2003/0120630 A1* 6/2003 Tunkelang ............ G06F 16/355
2003/0216919 A1* 11/2003 Roushar ................ G06F 40/284
704/260
(Continued)

*Primary Examiner* — Joy Chng
(74) *Attorney, Agent, or Firm* — Finnegan, Henderson, Farabow, Garrett & Dunner, LLP

(57) ABSTRACT

Systems and methods are provided for data driven analysis, modeling, and semi-supervised machine learning for qualitative and quantitative determinations. The systems and methods include obtaining data associated with individuals, and determining features associated with the individuals based on the data and similarities among the individuals based on the features. The systems and methods can label some individuals as exemplary, generate a graph wherein nodes of the graph represent individuals, edges of the graph represent similarity among the individuals, and nodes associated labeled individuals are weighted. The disclosed system and methods can apply a weight to unweighted nodes of the graph based on propagating the labels through the graph where the propagation is based on influence exerted by the weighted nodes on the unweighted nodes. The disclosed systems and methods can provide output associated with the individuals represented on the graph and the associated weights.

20 Claims, 10 Drawing Sheets

Related U.S. Application Data continuation of application No. 15/170,780, filed on Jun. 1, 2016, now Pat. No. 10,068,666.

(51) Int. Cl.

| | |
|---|---|
| ***G06F 16/28*** | (2019.01) |
| ***G06F 16/901*** | (2019.01) |
| ***G16Z 99/00*** | (2019.01) |
| ***G06Q 50/22*** | (2018.01) |
| ***G06F 16/35*** | (2019.01) |
| *G06Q 10/10* | (2023.01) |

(52) U.S. Cl.

CPC ............. *G16H 50/20* (2018.01); *G16Z 99/00* (2019.02); *G06F 16/355* (2019.01); *G06Q 10/10* (2013.01); *G06Q 50/22* (2013.01)

(58) Field of Classification Search

USPC .......................................................... 705/2–3

See application file for complete search history.

(56) References Cited

U.S. PATENT DOCUMENTS

| | | | | |
|---|---|---|---|---|
| 2006/0112146 | A1* | 5/2006 | Song | G06Q 10/10 |
| 2007/0203908 | A1* | 8/2007 | Wang | G06F 16/3331 707/E17.069 |
| 2011/0041075 | A1* | 2/2011 | Cierniak | G06Q 30/02 715/745 |

* cited by examiner

400

| | 410 | 420 | 430 | 440 | 450 | 460 |
|---|---|---|---|---|---|---|
| | Professional ID | Gender | Age | Location | Specialty | Affiliations |
| 401 | 1 | M | 54 | 94403 | Cardiology | PAMF |
| 402 | 2 | M | 60 | 92037 | Pediatrics | Scripps |
| 403 | 3 | F | 46 | 44195 | Orthopaedics | Cleveland Clinic |
| 404 | 4 | F | 70 | 85259 | Neurology | Mayo Clinic |
| 405 | 5 | M | 27 | 90048 | Internal Medicine | Cedar Sinai |
| | . | . | . | . | . | |
| | . | . | . | . | . | |
| | . | . | . | . | . | |
| | . | . | . | . | . | |
| | . | . | . | . | . | |
| 499 | N | M | 32 | 21287 | Ophthalmology | Johns Hopkins |

| | 510 | 520 | 530 | 540 | 550 | 560 | 570 | 580 |
|---|---|---|---|---|---|---|---|---|
| | Event ID | Person ID | Cost | Code 1 | Code 2 | Code 3 | Date | Professional ID |
| 501 | 1 | 1 | $8,000 | 409 | 10021 | R0076 | 1/1/2010 | 3 |
| 502 | 2 | 1 | $2,500 | 531 | 0001F | C9602 | 9/26/2012 | 3 |
| 503 | 3 | 1 | $100 | 461 | 47350 | A9152 | 7/27/2015 | 3 |
| 504 | 4 | 3 | $1,200 | 780.52 | 72345 | A9273 | 7/23/2005 | 3 |
| 505 | 5 | 5 | $180 | 787 | 99214 | G0009 | 3/17/2011 | 2 |
| 506 | 6 | 5 | $55 | 786.2 | 99213 | A4209 | 6/3/2013 | 5 |
| | . | . | . | . | . | . | . | . |
| | . | . | . | . | . | . | . | . |
| | . | . | . | . | . | . | . | . |
| | . | . | . | . | . | . | . | . |
| 599 | N | N | $150 | 523 | 97154 | G0205 | 2/5/2014 | 1 |

| | 610 | 620 | 630 | 640 | 650 | 660 |
|---|---|---|---|---|---|---|
| | Event ID | Product ID | Person ID | Cost | Date | Professional ID |
| 601 | 1 | 0573-0133 | 1 | $4,500 | 1/1/2010 | 3 |
| 602 | 2 | 29485-1887 | 1 | $5,500 | 9/26/2012 | 3 |
| 603 | 3 | 30142-027 | 1 | $325 | 7/27/2015 | 3 |
| 604 | 4 | 30142-055 | 3 | $500 | 7/23/2005 | 3 |
| 605 | 5 | 64406-011 | 5 | $1,000 | 3/17/2011 | 2 |
| 606 | 6 | 66758-050 | 5 | $60 | 6/3/2013 | 7 |
| | . | . | . | . | . | . |
| | . | . | . | . | . | . |
| | . | . | . | . | . | . |
| | . | . | . | . | . | . |
| 699 | N | ZZ | N | $150 | 2/5/2014 | 18 |

| | Professional ID | Feature 1 | Feature 2 | Feature 3 | Feature 4 | Feature 5 |
|---|---|---|---|---|---|---|
| 701 | 1 | 5 | 0 | 1 | 0 | 1.6 |
| 702 | 2 | 10 | 0 | 0 | 0 | 1.8 |
| 703 | 3 | 8 | 1 | 0 | 1 | 3.5 |
| 704 | 4 | 22 | 1 | 0 | 0 | 8.3 |
| 705 | 5 | 3 | 0 | 1 | 0 | 4 |
| | . | . | . | . | . | . |
| | . | . | . | . | . | . |
| | . | . | . | . | . | . |
| | . | . | . | . | . | . |
| | . | . | . | . | . | . |
| 799 | N | 99 | 1 | 0 | 0 | 0.85 |

Fig. 7

DATA DRIVEN ANALYSIS, MODELING, AND SEMI-SUPERVISED MACHINE LEARNING FOR QUALITATIVE AND QUANTITATIVE DETERMINATIONS

REFERENCE TO RELATED APPLICATIONS

This application is a continuation of U.S. patent application Ser. No. 16/119,018, filed on Aug. 31, 2018, which is a continuation of U.S. patent application Ser. No. 15/170,780, filed on Jun. 1, 2016, now U.S. Pat. No. 10,068,666 which is based upon and claims priority to the above disclosures of which are incorporated herein by reference in their entireties.

BACKGROUND

An ever increasing amount of data and data sources are now available to researchers, analysts, organizational entities, and others. This influx of information allows for sophisticated analysis to solve problems and draw conclusions, but in some areas, the availability of conclusions from this data is lacking.

Often, large data sets can contain data points falling into one or multiple known categories. The number of data points that are easily classifiable, however are often limited and do not provide practical benefit. Moreover, the remaining data points can often provide no clear indication regarding their appropriate categorization. Effective ways to expand the number of categorized data points can be time consuming and require large amounts of manual intervention.

Without effective data driven methods to analyze and expand the categorized data sets, users of the data sets cannot draw effective conclusions about the data as a whole.

BRIEF DESCRIPTION OF THE DRAWINGS

Reference will now be made to the accompanying drawings showing example embodiments of this disclosure. In the drawings:

FIG. 4 is an exemplary data structure consistent with embodiments of the present disclosure.

FIG. 5 is an exemplary data structure consistent with embodiments of the present disclosure.

FIG. 6 is an exemplary data structure consistent with embodiments of the present disclosure.

FIG. 7 is an exemplary data structure consistent with embodiments of the present disclosure.

DETAILED DESCRIPTION

Figure 1:
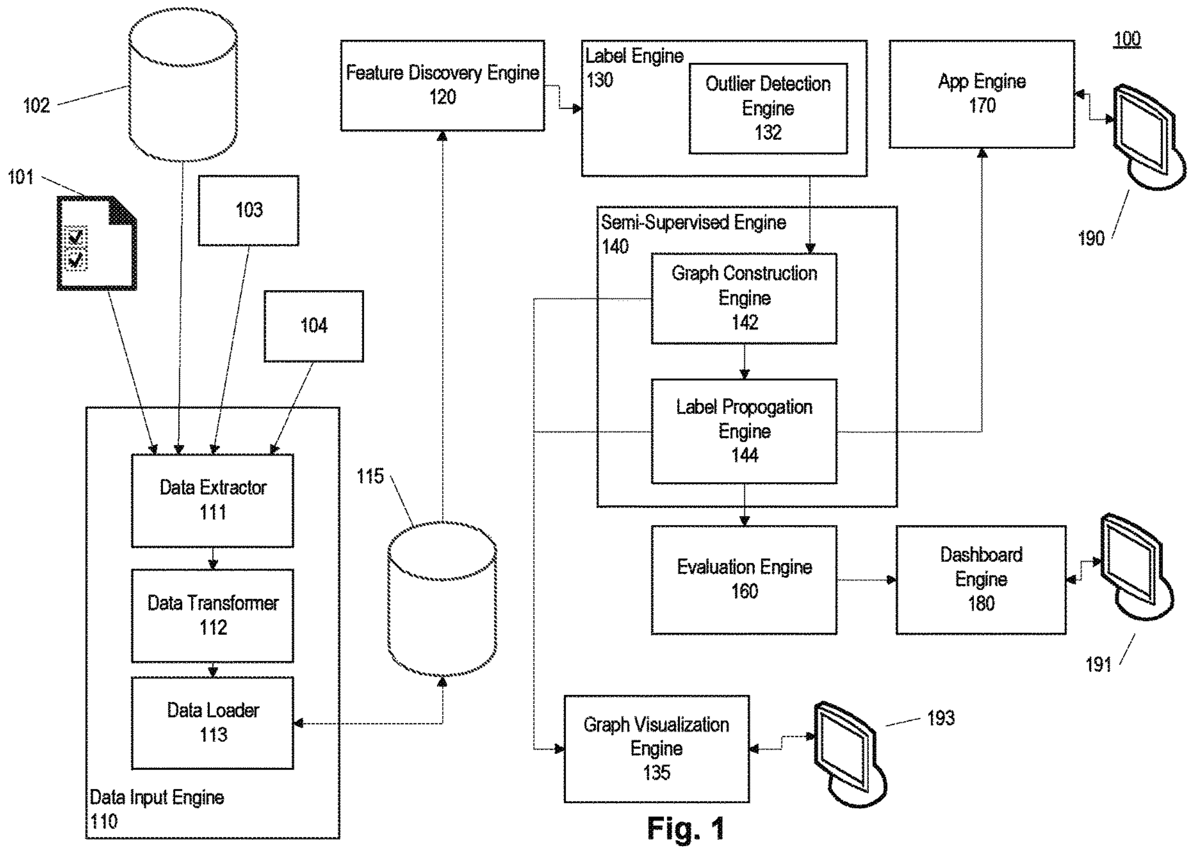
FIG. 1 is a block diagram of an exemplary system for data driven analysis, modeling, and semi-supervised machine learning, consistent with embodiments of the present disclosure.

Reference will now be made in detail to the exemplary embodiments implemented according to the present disclosure, the examples of which are illustrated in the accompanying drawings. Wherever possible, the same reference numbers will be used throughout the drawings to refer to the same or like parts.

The embodiments described herein relate to data driven analysis, modeling, and semi-supervised machine learning for qualitative and quantitative determinations. In many domains, determining good and bad professionals present a real challenge. Often, websites or forums are used where consumers can post and read reviews. Often, particularly in domains such as healthcare, these reviews can be highly subjective and based on criteria that may not be important to the reader. Moreover, in some domains, like healthcare, there are often very few if any reviews for a given physician. Choosing a good or bad doctor can be further complicated by the need to ensure that a physician accepts certain insurance payments. Even if a patient finds a good doctor based on reviews, that doctor may not accept the patient's insurance.

Some systems have attempted to solve these problems, but those systems similarly rely on faulty or unreliable information. For example, some methods for establishing physician quality can rely on academic credentials. These methods, however, are biased against physicians who may be excellent but do not have a degree from an esteemed medical school. Additionally, reliance on criteria like academic credentials or demographics uses a false assumption that all physicians who went to a highly regarded medical school are necessarily good doctors.

The embodiments disclosed herein approach these problems from a different perspective. Instead of making broad assumptions based on small amounts of data, the disclosed systems and methods process vast amounts of data and use data driven approaches of analysis, such as semi-supervised machine learning to identify good and bad doctors. Instead of only analyzing small, discrete elements of a physician's background or history, the disclosed system places no limit on the amount or type of information that is available for analysis. In addition to demographic information, the disclosed system and methods can utilize claims data, prescription data, scholarship, patient feedback, proprietary information, and any other available data. The systems disclosed can process that data in an efficient and effective way to create data structures that can be used to group physicians who are similar not only by where they went to school, but by countless factors culled from the available data.

After exemplary good and bad doctors are found, additional doctors who display similar characteristics can further be added. These physicians, that represent only a small number of the physicians a patient might see, can then be analyzed by applying concepts such as electrostatic modeling and point charge propagation to model how similarities among the physicians affect determinations about quality. Although the analysis can utilize both subjective and objective data inputs, the modeling allows for determinations to be made without traditional biases, like subjective quality of medical school, affecting the identification of good and bad doctors. Using this process, users of the system can draw conclusions about the quality of a vast number of physicians from known information about a few. Patients can be provided with much better information about physicians in their insurance networks without relying on unreliable information like minimal reviews and insurance network providers can utilize this system to ensure they cover high quality physicians.

The embodiments described herein provide technologies and techniques for using vast amounts of available data (originating from different data sources) to drive analysis, modeling, and semi-supervised machine learning approaches to make determinations about the quality of professionals in a field. Embodiments described herein include systems and methods for obtaining, from one or more data sources, one or more data sets associated with a plurality of individuals and determining features associated with the plurality of individuals wherein the features are based on data in the one or more data sets among the plurality of individuals. The embodiments herein further include labeling a subset of the plurality of individuals as exemplary, determining similarities among the plurality of individuals, wherein the determination of similarities is based on an evaluation of the determined features, generating data representing a graph having a plurality of nodes, wherein nodes of the graph are associated with the plurality of individuals, edges between the nodes represent the determined similarities, wherein the nodes include unweighted node and weighted nodes, applying a weight to unweighted nodes of the graph, wherein the weights are based on an influence exerted by the weighted nodes on the unweighted nodes, providing output associated the graph and the associated weights.

In additional embodiments, the systems and methods disclosed further include a graph that is fully connected. Additional embodiments can include utilizing a random graph model to select a subset of individuals to connect using edges which can alleviate noise and over complexity. Some embodiments disclosed herein can include weighted edges on the graph and labeling one or more of the individuals as positive or negative. The individuals chosen as positive or negative labels can be exemplary good or bad professionals in their field.

In yet other embodiments consistent with the present disclosure, the system and methods can include labeling a first set of individuals of the plurality of individuals as exemplary wherein the first set of individuals includes at least one individual that is associated with a subset of features and wherein the subset of features correlate to qualities associated with exemplary individuals. In these embodiments the system and methods can further identify a second set of individuals of the plurality of individuals that are similar to at least one individual of the first set wherein the similarity is based on features associated with the at least one individual and the second set of individuals. In these embodiments, the second set of individuals can also be exemplary labels or labeled as exemplary.

In additional embodiments, the weighted or labeled nodes of the graph can be treated as positive or negative point charges and the influence exerted by the weighted nodes on the unweighted nodes can be calculated by calculating the electrical potential associated with those nodes. In these embodiments, the graph can be analyzed using electrostatic modeling and apply Poisson's equation, Laplace's equation, a Laplacian exponential diffusion kernel, a regularized Laplacian kernel, or a von Neumann diffusion kernel to the graph.

In some embodiments, after weights are determined for all of the nodes, the individuals associated with those weights and the weights can be provided for display on a graphical user interface, or for further processing and use by a client device or other components of the system.

The embodiments described herein can apply to many fields. Descriptions and applications related to specific domains do not preclude the application of the described embodiments to other technologies of fields.

FIG. 1 is a block diagram representing exemplary system 100 for data driven analysis and modeling consistent with embodiments of the present disclosure. System 100 can include data input engine 110 that can further include data extractor 111, data transformer 112, and data loader 113. Data input engine 110 can process data from data sources 101-104. Data input engine 110 can be implemented using computing device 200, described in more detail below in reference to FIG. 2. For example, data from data sources 101-104 can be obtained through I/O devices 230 and/or network interface 218 of computing device 200. Further, the data can be stored during processing in a suitable storage such as storage 228 and/or system memory 221. Referring back to FIG. 1, data input engine 110 can also interact with data storage 115. Data storage 115 can further be implemented on a computing device such as computing device 200, described in detail below in FIG. 2, that stores data in storage 228 and/or system memory 221. In some embodiments, data storage 115 can be remote from computing device 200.

Referring back to FIG. 1, system 100 can include feature discovery engine 120, label engine 130, graph visualization engine 135, semi supervised engine 140, graph construction engine 142, label propagation engine 144, evaluation engine 160, app engine 170, and dashboard engine 180. System 100 can further include output terminals or displays 190, 191, and 193. Similarly to data input engine 110, these various components can be implemented on a computing device such as computing device 200, can utilize storage 228 and/or system memory 221 for storing data, and can utilize I/O device 230 or network interface 218 for transmitting and/or receiving data, all described in more detail below in reference to FIG. 2. Each of data input engine 110, data extractor 111, data transformer 112, data loader 113, feature discovery engine 120, label engine 130, graph visualization engine 135, semi-supervised engine 140, graph construction engine 142, label propagation engine 144, evaluation engine 160, app engine 170, and dashboard engine 180 can be a module, which is a packaged functional hardware unit designed for use with other components or a part of a program that performs a particular function of related functions. Each of these modules can be implemented using computing device 200 of FIG. 2. Each of these components is described in more detail below. In some embodiments, the functionality of system 100 can be split across multiple computing devices (e.g., multiple devices similar to computing device 200) to allow for distributed processing of the data. In these embodiments the different components can communicate over I/O device 230 or network interface 218 of FIG. 2's computing device 200.

System 100 can be related to many different domains or fields of use. Descriptions of embodiments related to specific domains, such as healthcare, is not intended to limit the disclosed embodiments to a specific domain, and embodiments consistent with the present disclosure can apply to any domain that utilizes predictive modeling based on available data.

Data input engine 110 is a module that can retrieve data from a variety of data sources (e.g., data source 101, 102, 103, and 104) and process the data so that it can be used with the remainder of system 100. Data input engine 110 can further include data extractor 111, data transformer 112, and data loader 113.

Data extractor 111 retrieves data from data sources 101, 102, 103, and 104. Each of these data sources can represent a different type of data source. For example, data source 101 can be a database. Data source 102 can represent structured data. Data sources 103 and 104 can be flat files. Further, data sources 101-104 can contain overlapping or completely disparate data sets. In some embodiments, data source 101 can contain individual information while data sources 102, 103, and 104 contain various insurance claim and medical treatment data. For example, data source 101 can contain data structure 400, 500, and 600 of FIGS. 4, 5, and 6. Data extractor 111 can interact with the various data sources, retrieve the relevant data, and provide that data to data transformer 112.

Data transformer 112 can receive data from data extractor 111 and process the data into standard formats. In some embodiments, data transformer 112 can normalize data such as dates. For example data source 101 can store dates in day-month-year format while data source 102 can store dates in year-month-day format. In this example, data transformer 112 can modify the data provided through data extractor 111 into a consistent date format. Accordingly, data transformer 112 can effectively clean the data provided through data extractor 111 so that all of the data, although originating from a variety of sources, has a consistent format.

Moreover, data transformer 112 can extract additional data points from the data. For example, data transformer can process a date in year-month-day format by extracting separate data fields for the year, the month, and the day. Data transformer can also perform other linear and non-linear transformations and extractions on categorical and numerical data such as normalization and demeaning. Data transformer 112 can provide the transformed and/or extracted data to data loader 113.

Data loader 113 can receive the normalized data from data transformer 112. Data loader 113 can merge the data into varying formats depending on the specific requirements of system 100 and store the data in an appropriate storage mechanism such as data storage 115. In some embodiments, data storage 115 can be data storage for a distributed data processing system (e.g., Hadoop Distributed File System, Google File System, ClusterFS, and/or OneFS). In some embodiments, data storage 115 can be a relational database (described in more detail below). In additional embodiments data storage 115 can be a graph database (e.g., Neo4j or Titan) Depending on the specific embodiment, data loader 113 can optimize the data for storing and processing in data storage 115. In some embodiments, data structures 400, 500, and 600 from FIGS. 4, 5, and 6 (or versions thereof) can be stored by data loader 113 in data storage 115.

Feature discovery engine 120 can process the data prepared by data input engine 110 and stored in data storage 115. Feature discovery engine can retrieve data from data storage 115 that has been prepared by date input engine 110. For example, data structures 400, 500, and 600 of FIGS. 4, 5, and 6 can be suitable inputs to feature discovery engine 120.

As shown in FIG. 4, data structure 400 is an exemplary data structure, consistent with embodiments of the present disclosure. Data structure 400 can store data records associated with professionals. While data structure 400 is shown to store information related to physicians, it is appreciated that it can store information related to any profession. Data structure 400 can, for example, be a database, a flat file, data stored in memory (e.g., system memory 221), and/or data stored in any other suitable storage mechanism (e.g., storage 228).

In some embodiments, data structure 400 can be a Relational Database Management System (RDBMS) (e.g., Oracle Database, Microsoft SQL Server, MySQL, PostgreSQL, and/or IBM DB2). An RDBMS can be designed to efficiently return data for an entire row, or record, in as few operations as possible. An RDBMS can store data by serializing each row of data of data structure 400. For example, in an RDBMS, data associated with record 401 of FIG. 4 can be stored serially such that data associated with all categories of record 401 can be accessed in one operation. Moreover, an RDBMS can efficiently allow access of related records stored in disparate tables. For example, in an RDBMS, data structure 400 of FIG. 4 and data structure 500 (described in more detail below) of FIG. 5 can be linked by a referential column. In this example, professional ID 580 of data structure 500 can directly relate to professional ID 410 of data structure 400. An RDBMS can allow for the efficient retrieval of all records in data structure 500 associated with a record of data structure 400 based on a common value for the respective professional ID fields (e.g., professional ID 580 of data structure 500 and professional ID 410 of data structure 400).

In some embodiments, data structure 400 of FIG. 4 can be a non-relational database system (NRDBMS) (e.g., XML, Cassandra, CouchDB, MongoDB, Oracle NoSQL Database, FoundationDB, and/or Redis). A non-relational database system can store data using a variety of data structures such as, among others, a key-value store, a document store, a graph, and a tuple store. For example, a non-relational database using a document store could combine all of the data associated with a particular professional ID (e.g, professional ID 410 of data structure 400 and professional ID 580 of data structure 500 in FIG. 5) into a single document encoded using XML. In this example, the XML document would include the information stored in record 402 of data structure 400 and record 505 of data structure 500 based on these records sharing the same professional ID value.

Data structure 400 of FIG. 4 can include data records 401-405 representing physicians in addition to countless additional records up to record 499. Data structure 400 can contain many thousands or millions of records of data and is limited only by the physical constraints of the system upon which the data structure exists.

Data structure 400 can include categories of data representing a physician. For example data structure 400 can include categories professional ID 410, gender 420, age 430, location 440, specialty 450, and affiliations 460. Data associated with data records 401-405 can be stored under each of these categories. For example, a physician represented by data record 401 has a person ID of "1," is male as represented by an "M" under gender 420, is 54 as listed under age 430, works in zip code "94403" as represented under location 440, specializes in cardiology as represented under specialty 450, and is affiliated with the Palo Alto Medical Foundation (PAMF) as represented by affiliations 460.

In some embodiments, data structure 400 can contain more or fewer categories for each data record. For example, data structure 400 can include additional categories of data such as certifications, education, publications, or any other category of data associated with a professional. Moreover, depending on the circumstances, data structure 400 can contain domain specific data. For example, in a healthcare context, in addition to healthcare specific specialty 450 and affiliations 460 data, data structure 400 can include insurance coverage information, practice or group name, teaching positions, or other information related to a physician. Accordingly, data structure 400 is not limited to only those categories shown in FIG. 4.

In some embodiments, data structure 400 contains categories that store similar data. For example, data structure 400 can include location 440 that represents a business address zip code, while an additional "location" category (not shown) can be used to store a secondary business zip code. In some embodiments, categories, such as location, can be stored in multiple normalized tables. For example, a separate table representing physician locations could store all of the location information for a physician in a separate data structure or, in the context of a relational database, a table, using multiple records. These disparate data sets or tables can include referential categories that can be used to join the data.

Additionally, data structure 400 can include combination categories. For example, instead of only using location 440 to represent location information, data structure 400, in some embodiments, includes categories for, among others, street address, state, city, and/or country. This data can be stored under one category or separate categories that, together, represent a location.

Moreover, location 440 can store different types of data. In some embodiments, location 440 is a zip code. In other embodiments, location 440 is a combination category as previously described. Location 440 can further include, geospatial coordinates, map coordinates, or any other data type that indicates location.

Similarly to location 440, other categories, such as age 430, specialty 450, and affiliations 460, can include data in a variety of formats. For example, age 430 can be represented in years, in years and months, in days, or by a date of birth.

In some embodiments, data stored under a category can be a reference into another data set or data structure as is common in relational data sets. For example, specialty 450 and affiliations 460 can contain an identifier that references a description stored in a separate data set or lookup table instead of containing text or another data type.

Additionally, as shown in FIG. 5, data structure 500 is an exemplary data structure, consistent with embodiments of the present disclosure. Data structure 500 can store data records associated with events that are further associated with specific individuals. Similarly to data structure 400 described in FIG. 4, data structure 500 can, for example, be a database, a flat file, data stored in memory (e.g., system memory 221 of computing device 200 from FIG. 2), an RDBMS, an NRDBMS, and/or data stored in any other suitable storage mechanism (e.g., storage 228 of computing device 200 from FIG. 2). Moreover, data structure 500 can be implemented or stored computing device similar to computing device 200 described in FIG. 2.

Data structure 500 can store information related to events. Data structure 500 can include data records 501-506 representing data associated with specific events in addition to countless additional records up to record 599. Data structure 500 can contain millions or billions of records of data and is limited only by the physical constraints of the system upon which the data structure exists.

Data structure 500 can include categories of data. For example, data structure 500 can include the categories event ID 510, person ID 520, cost 530, code 1 540, code 2 550, code 3 560, date 570, and professional ID 580. Data associated with data records 501-506 can be stored in each respective row of data structure 500 within one of these categories. For example, an event represented by data record 501 is associated with a person ID 520 of "1," has a cost 530 of "$8000," has values of "409," "10021," and "R0076," for code 1 540, code 2 550, and code 3 560, respectively, a date 570 of "1/1/3010," and a professional ID 580 of "3." In some embodiments multiple professional ID categories can be included in the data structure to indicate the involvement of multiple physicians. In other embodiments, multiple professional ID categories can be included to indicate different roles. In a healthcare context, data structure 500 can include categories for a professional ID for a referring physician, rendering physician, and supervising physician.

Moreover, data structure 500 can include multiple data records associated with the same individual or professional. For example, data records 501-503 all have a value of 1 for person ID 520. Moreover, data records 501-504 all have a value of 3 for professional ID 580. These values can refer to a person ID number or professional ID number stored in a separate data set. For example, professional ID 580 can refer to professional ID 410 of data structure 400 described in FIG. 4. In this example, data records 501-504 of data structure 500 can be associated with data record 403 of data structure 400. Moreover, data record 505 of data structure 500 can be associated with data record 402 of data structure 400 and data record 506 of data structure 500 can be associated with data record 405 of data structure 400 based on the values in professional ID 580 and professional ID 410 of data structure 400 in FIG. 4.

In some embodiments, the data records in data structure 500 are all related to the same type of event or a specific domain. For example, data structure 500 can contain data records related to medical insurance claims. In these embodiments, data structure 500 includes additional categories that are specific to these types of events or domains, such as categories for deductibles. Moreover, in these embodiments, existing categories may contain information related to the domain of the data. For example, in embodiments where data structure 500 includes health insurance claim data, code 1 540, code 2 550, and code 3 560 can represent International Statistical Classification of Diseases and Related Health Problems (ICD) codes, Current Procedural Terminology (CPT) codes, and Healthcare Common Procedure Coding System (HCPCS) codes respectively. Additionally, these types of codes can represent hierarchical data. Accordingly, a specific code in one of code 1 540, code 2 550, or code 3, 560 may imply additional codes or procedures based on the specific classification system in use. In a different domain, code 1 540, code 2 550, and code 3 560 can represent different identifying information for the events represented in data structure 500.

Similarly to data structure 400, data structure 500 can include more or fewer categories for each data record depending on the domain and the source of the data record. Additionally, as described in relation to data structure 400, some categories of data structure 500 can store data in different formats that represent the same concept, such as a date or cost. For example, date 570 can contain only a month and year, or can contain month, day, and year. In a similar example, cost can contain values in terms of United States Dollars or in terms of other currencies.

Additionally, as shown in FIG. 6, data structure 600 is an exemplary data structure, consistent with embodiments of the present disclosure. Data structure 600 can store data records associated with events that are further associated with specific individuals. Similarly to data structure 400 and data structure 500 described in FIGS. 4 and 5, data structure 600 can, for example, be a database, a flat file, data stored in memory (e.g., system memory 221 of computing device 200 from FIG. 2), an RDBMS, an NRDBMS, and/or data stored in any other suitable storage mechanism (e.g., storage 228 of computing device 200 from FIG. 2). Moreover, data structure 600 can be implemented or stored in a computing device similar to computing device 200 described in FIG. 2.

Data structure 600 can store information related to events associated with a product. For example, event could be the purchase of a product, or in the domain of healthcare, prescription information related to a drug. Data structure 600 can include data records 601-606 representing data associated with a specific event in addition to countless additional records up to record 699. Data structure 600 can contain millions or billions of records of data and is limited only by the physical constraints of the system upon which the data structure exists.

Data structure 600 can include categories of data. For example, data structure 600 can include the categories event ID 610, product ID 620, person ID 630, cost 640, date 650, and professional ID 660. Data associated with data records 601-606 can be stored in each respective row of data structure 600 within one of these categories. For example, an event represented by data record 601 is associated with a product ID 620 of "0573-0133," person ID 630 of "1," has a cost 640 of "$4,500," a date 650 of "1/1/2010," and a professional ID 680 of "5." In this example, product ID 620 can be a reference to the ID for a drug listing in the National Drug Code (NDC) database, and data record 601 can represent a prescription for a medication, such as Advil®. Moreover, data structure 600 can include multiple data records associated with the same individual or professional. For example, data records 601-603 all have a value of "1" for person ID 630. Moreover, data records 601-604 all have a value of 3 for professional ID 680. These values can refer to a person ID number or professional ID number stored in a separate data set. For example, professional ID 680 can refer to professional ID 410 of data structure 400 described in FIG. 4. In this example, data records 601-604 of data structure 600 can be associated with data record 403 of data structure 400. Moreover, data record 605 of data structure 600 can be associated with data record 402 of data structure 400 based on the values in professional ID 680 and professional ID 410 of data structure 400 in FIG. 4.

In some embodiments, the data records in data structure 600 are all related to the same type of event or a specific domain. For example, data structure 600 can contain data records related to drug prescription claims. In these embodiments, data structure 600 includes additional categories that are specific to these types of events or domains, such as categories for deductibles. Moreover, in these embodiments, existing categories may contain information related to the domain of the data. For example, in embodiments where data structure 600 includes drug prescription claim data, product ID 620 can represent National Drug Codes (NDC) that are part of the National Drug Code Directory.

Similarly to data structure 400 and data structure 500, data structure 600 can include more or fewer categories for each data record depending on the domain and the source of the data record. Additionally, as described in relation to data structures 400 and 500, some categories of data structure 600 can store data in different formats that represent the same concept, such as a date or cost. For example, date 650 can contain only a month and year, or can contain month, day, and year. In a similar example, cost can contain values in terms of United States Dollars or in terms of other currencies.

Referring back to FIG. 1, feature discovery engine 120 can process the data from data storage 115. This data can be stored using data structures such as data structures 400, 500 and 600, described above in relation to FIGS. 4, 5, and 6. From this data, feature discovery engine 120 can determine features that describe the data.

A feature can be data that is representative of other data. Features can be determined based on the domain, data type of a category, or many other factors associated with data stored in a data structure. Additionally, a feature can represent information about multiple data records in a data set or information about a single category in a data record. Moreover, multiple features can be produced to represent the same data.

A feature can be based on the data type stored for a category. A category that stores real numbers, for example, can be represented by a feature generated using functions such as minimum, maximum, average, or mean across multiple data sets. For example, a feature representing the maximum cost charged by physician for a medical procedure can be based on the cost 530 category of data structure 500 in FIG. 5. In this example, data records 501-504 represent medical procedures performed by the same physician. A feature representing the maximum cost charged by that physician can be calculated by comparing the cost values of "$8000," "$2500," "$100," and "$1200" stored in data records 501-404 and determining that "$8000" is the maximum value. This type of feature can be determined for only those records pertaining to the same physician or can be determined across a data set representing claims for multiple physicians.

One set of data points can produce multiple features related to that data. For example, in addition to calculating the maximum cost for data records 501-504 of FIG. 5, features representing the average cost, minimum cost, mean cost, or cost distribution can also be determined from the same cost category of data records 501-504. In the case of a distribution, multiple features can be generated that represent the different aspects of or summarize the distribution. For example, the distribution of the cost stored in data records 401-403 can result in features that describe the skew, kurtosis, entropy among other distribution related measurements of the cost data.

In addition to features associated with real numbers, features can be based on categorizations. Categorizations can include a count of data points, specific data indicators, most frequent types of data points, or similar features. In some embodiments, in relation to healthcare data, categories can include the most expensive claim, the count of claims, particular claims known to be indicators of a specific condition, for example, a heart attack, a specific category of ICD or CPT codes, the most frequent code in the claims data, or many additional characteristics of the claims data. Each of these categories can be established as a feature.

Moreover, features can be established based on dates. In some embodiment related to healthcare and claims data, features can include the duration of certain types of claims or treatments, the onset date of a particular type of claim, or similar date data.

Features can also be based on data not directly included in the data records. In a healthcare context, for example, code 1 540, code 2 550, and code 3 560 can represent specific codes, such as ICD, CPT, or HCPCS codes that represent specific treatments. These codes can be part of a larger hierarchical system. For example, a code that represents the treatment of high insulin levels may implicitly indicate treatment for diabetes although only the code for high insulin is included in the data record. Because of the hierarchical nature of the coding system, feature discovery engine 120 can determine that a claim for high insulin includes both a feature for the treatment of high insulin as well as a feature representing the treatment of diabetes. In another example, data records can contain a reference, such as a National Provider Identifier (NPI), that identifies a provider. In this example, the provider information can be joined with the data records providing additional data and information for determining features. This sort of external data can be stored in, for example, data storage 115 of FIG. 1 and available to feature discovery engine 120. These examples and descriptions of features are not exhaustive. Features can be any data descriptive of the data stored in a record and feature discovery engine 120 can generate a data structure to store the determined features.

As shown in FIG. 7 data structure 700, is an exemplary data structure, consistent with embodiments of the present disclosure. Data structure 700 can use a representation of features related to professional created by feature discovery engine 120. Similarly to data structure 400 described in FIG. 4, data structure 500 described in FIG. 5, and data structure 600 described in FIG. 6, data structure 700 can, for example, be a database, a flat file, data stored in memory (e.g., system memory 221 of computing device 200), an RDBMS, an NRDBMS, and/or data stored in any other suitable storage mechanism (e.g., storage 228 of computing device 200). Moreover, data structure 700 can be implemented or stored on a system similar computing device 200 as described in FIG. 2.

Data structure 700 can store feature information related to professionals. Data structure 700 can include data records 701-705 representing individuals in addition to countless additional records represented by records up to record 799. Data structure 700 can contain many millions or billions of records of data and is limited only by the physical constraints of the system upon which the data structure exists. Moreover, data structure 700 can include many thousands of feature categories in addition to feature categories Feature 1, Feature 2, Feature 3, Feature 4, and Feature 5.

Similarly to data structure 500 in FIG. 5 and data structure 600 in FIG. 6, professional ID 710 of FIG. 7 can be a reference to data structure 400 of FIG. 4. Accordingly data record 701 can represent data about the same professional as data record 401 of data structure 400 based on the Professional ID of each respective data structure. Moreover, as will be demonstrated below, values associated with feature categories Feature 1 through Feature 5 can be based on data contained in additional data structures such as data structure 500 of FIG. 5 and data structure 600 of FIG. 6. Thus, data structures 400, 500, 600 and 700 of FIGS. 3, 4, 5 and 6, respectively, can all be linked based on the professional ID categories 410, 580, 660 and 710, respectively. Moreover, each feature category, Feature 1 through Feature 5 can correspond directly to features identified and/or calculated by feature discovery engine 120.

After a feature is established and/or calculated as described above (e.g., by feature discovery engine 120) the feature can be processed into a binary value and stored in data structure 700. Data records 701-706 can include this binary data associated with each feature category. For example, data record 701 includes a "5" value for Feature 1, a "0" value for Feature 4 and a "1" value for Feature 2 and Feature 3, and a "1.6" value for Feature 5. A zero value for a feature category can indicate that the individual referenced by professional ID 710 for the data record does not have that particular feature while a one value for a feature category can indicate that the individual referenced by person ID 710 does have that feature. As shown in record 701, different data types can be used for features. As shown features can include binary data, real number data, integer data, as well as a variety of other data types and is not limited to just those shown in data structure 700.

For example, Feature 2 can represent a feature of "Female." As shown above, person ID 710 can be a reference to additional data structures such as data structure 400 described in FIG. 4. Data records 403 and 404 of data structure 400 include a value of "F" for gender 420. Accordingly, because data records 703 and 704 can refer to data records 403 and 404 based on having the same value for professional IDs 410 and 710, data records 703 and 704 can contain a "1" value for the feature of "Female." In this example, because an individual can only be male or female, data records 701, 702, and 705 represent individuals who are male based on the zero value for Feature 2. In some embodiments, a separate feature category can be used to represent a "Male" feature.

In another example in a healthcare context, Feature 4 can be a feature representing "Physicians who have written more than one prescription." Moreover, data structure 600 can represent prescription data. Because data structure 700 can be associated with data structure 600 based on the values of professional ID 710 and 660, the data in data structure 600 can be used to populate values for Feature 4 of data structure 700. As shown in FIG. 6, data records 601-604 are associated with Professional ID "3" and data records 605 and 606 are associated with Professional IDs "2" and "7," respectively. Accordingly, because data records 601-604 of data structure 600 are all associated with a physician having a professional ID of 3, that particular physician has written 4 prescriptions. Because Feature 4 of data structure is "physicians who have written more than one prescription," data record 703 can contain a "1" value to indicate that, based on the prescription data in data structure 600, the physician referred to in data record 703 has written more than one prescription.

Various other features can be created based on any available date. Many of these features can be domain specific. For example, in a healthcare context, features can be used to indicate medical schools, residencies, hospital affiliations, board memberships, claims analytics, specialties, the number of patients treated, the specific diseases treated or treatment codes used, the amount billed, the number of referrals or times referred, the physicians role for particular treatments (e.g., as a referring physician, rendering physician, or both), or any other type of information that can be used to categorize or describe a physician.

Further features can include analytics of the various types of data. These analytics can further be broken down by category. For example, if a claim data associated with a physician includes referrals, renderings, and both (e.g., a self-referral), individual analytics for the physician can be included for each of these roles. These various analytics, as well as overall analytics can be expressed as various features in data structure 700.

Additionally, feature discovery engine 120 can produce multiple binary features based on one or more specific non-binary features. For example, quantile binning or hashing techniques can be used to classify categorical data. Data that represents a range or duration can be represented by the quantile bin with which that range corresponds.

For example, in a healthcare context, claim data related to the treatment of chest pain may indicate that different specific professionals treated chest pain by ordering different types of test. In this example, if the range of the number of tests ordered that are represented in the data set is between 0 and 100 tests, a binary representation of the number of tests feature can be obtained by splitting the possible range into 4 groups of 25 tests each. Further, in this example, each representation of the feature can include a feature category for each of the four groups with a "1" value for the specific number range that relates to the number of tests ordered by that physician for treatment of a patient's chest pain and a "0" value for all other numbers for that physician. For example, a physician who ordered 40 tests for chest pain could have a "0" for feature categories representing number of tests ranges of 1-25 tests, 51-75 tests, and 76-100 tests and a "1" value for the feature category representing 26-50 tests. The number of bins used can be increased or decreased based on the specific data type, the data represented, the specific domain, or other factors. In some embodiments, the same total number data could be processed using multiple bin sets. For example, total number data could be processed using a 4 bin set as well as processed using a 10 bin set. The binary output from both sets of processing can be stored for the individual and included as part of the later analysis.

After processing the data, feature discovery engine 120 can produce feature data, which can be stored in data storage 215 for later analysis or passed directly to other components of the system. The feature data included can be based on automated processes or can be based on a pre-determined set of features.

The feature discovery engine 120 can provide the generated feature data to label engine 130. From the data set, label engine 130 can select professionals as positive or negative examples of the members of their profession. In a healthcare context, label engine 130 can identify good and bad physicians and use those identified physicians as labels. The specific criteria for determining good and bad is described in more detail below and can be based on domain specific factors. In the following discussion, the examples of using physician data are exemplary only, and the same technique can be used in many different domains.

Label engine 130 can analyze the feature data provided by feature discovery engine 120. From this data, and based on characteristics of the specific domain, certain signal features can be used to indicate outliers in both a positive and negative direction for the given domain. For example, in a healthcare context, physician labels can be created for good and bad doctors. Although good and bad can be subjective determinations, certain features can be used to indicate the level of quality of doctors.

Label engine 130 can include outlier detection engine 132. Outlier detection engine 132 can discover outliers in the data set that are clearly positive or negative examples of the quality of doctors. These determinations can be made by a manual identification if the specific physician. Additionally, certain defined characteristics can be an indication that a specific physician is an exemplary positive or negative label. In some embodiments, outlier detection engine 132 is a separate component from label engine 130.

In addition to outlier detection engine 132, label engine 130 can rely on the feature data to determine labels. For example, some of the feature data may indicate that a particular physician produces a large number of Relative Value Units ("RVUs"). RVUs are a measure that is used for Medicare reimbursement. A high number of RVUs billed can indicate that a physician is well compensated, which can further indicate high quality. These types of metrics can further be controlled based on other features or demographics. RVU measurements can be unhelpful when comparing a general practice physician to a specialist but when comparing two physicians in the same specialty and/or subspecialty, RVUs can provide an indicator of quality. Additionally, features can indicate the amount that a physician publishes in their field. Active community participation and scholarship in an area of specialty can further indicate the quality of the physician. Many other types of features can be used. In some embodiments, features indicating board certifications, group memberships, or similar accomplishments can indicate quality. Additional measures of physician performance, like the number of procedures performed, the type of procedures performed, and the number of complications can further indicate quality.

Conversely, features can also indicate physicians that are considered lower quality. For example, features can indicate the number of ethical violations, reprimands, malpractice proceedings, patient complaints, or similar negative actions taken against a physician. This type of feature may indicate physicians considered to be of lower quality. Additional features could include statistics like patient turnover. Similarly to the positive features, these statistics can be controlled based on specialty type because some specialties or types of physicians may naturally have higher patient turnover. Similarly to considering high levels of publishing as a positive feature, low levels of publishing can be considered a negative feature. This can be especially true if the level of publishing is compared to the averages for physicians or physicians in that particular specialty. Moreover, physician behavior and claim information can further indicate quality level. For example, if the over prescription of certain tests for a particularly condition indicates lower quality care, features indicating the overuse of that particularly test can be used to identify physicians of lower quality.

Additionally, multiple sets of features can be used to classify professionals. Referring again to physicians, while metrics, such as attending a respected medical school or a securing a selective fellowship, can help identify high quality physicians, there are potentially many other physicians who are high quality but would not have these features. These physicians, however, may be active in the community or account for a high level of RVUs. By using multiple sets of features, different types of physicians can be identified. For example, a particular doctor could hold a record for the highest number of complex coronary interventions performed annually, hold a record for the highest angioplasty success rate in New York, and have her own Wikipedia page, but she did not attend a United States medical school. Traditional methods for determining quality that highly favor medical school would not consider that doctor a high quality physician although based on her practice history she would likely be considered a high quality physician. Accordingly, using features that represent different types of data can lead to better identification of physicians as high or low quality and whose designations can be based on different criteria.

In some embodiments, multiple features represent the same idea. For example, experience can be represented by features for the number of procedures performed and also years of experience. In these embodiments, number of procedures performed can be a better signal of high or low quality even though both features are a measure of experience.

The specific features and combination of features described above are exemplary. Any features produced by feature discover engine 120 can be used to determine both good and bad exemplary professionals. As more data is considered and modeled, system 100 can adjust the features used based on evaluation of the system's output. This evaluation is discussed in more detail below.

After an initial set of high quality and low quality professionals are identified, label engine 130 can designate these professionals as labels. Label engine 130 can then proceed to expand the labels to other professionals in the data set. The initial goal of assigning labels is to identify a core set of high and low quality professionals. Various techniques can then be used to expand the labels to other professionals in the data set to allow for a sufficient amount of data for the next steps in the process implemented by system 100.

Label engine 130 can use the initial set of identified professionals and further identify nearest neighbors. By treating the feature list as a vector representing each physician, various statistical analysis approaches can be used to find the nearest neighbors to the already identified professionals. The number of additional neighbors used can depend on the number of professionals initially identified by label engine 130.

In some embodiments, label engine 130 can use locality sensitive hashing to find nearest neighbors. This approach can provide increases in processing feed. Additional embodiments can randomly select subsets of neighbors. In yet another embodiment, a brute-force approach can be used to find nearest neighbors. In these embodiments, the distances of all pairwise neighbors are computed. These embodiments can provide the most accurate results but at a significant computational complexity.

Semi-supervised engine 140 can include components that implement semi-supervised learning approaches for analyzing the available data set. In particular, semi-supervised engine 140 can consist of graph construction engine 142 and label propagation engine 144. The inclusion of graph construction engine 142 and label propagation engine 144 in semi-supervised engine 140 is only exemplary. In some embodiments these modules are implemented or represented as separate and distinct components.

Graph construction engine 142 can generate a graph representation of the professionals represented in the feature data. Graph construction engine 142 can combine the feature data with the labels determined by label engine 130 to create a connected graph. Graph construction engine 142 can build a graph based on similarities among the professionals in the feature data and place the appropriate labels on that graph.

Figure 8:
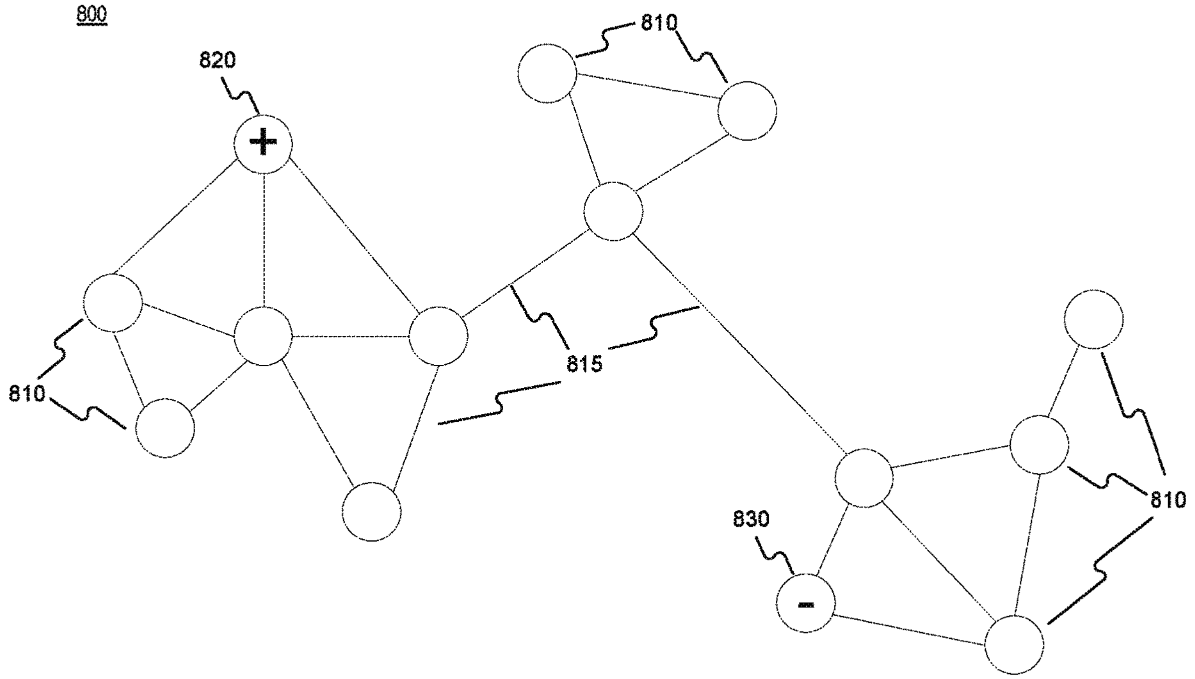
FIG. 8 is an exemplary graph consistent with embodiments of the present disclosure.

As shown in FIG. 8, graph 800 can represent a graph consistent with embodiments of the present disclosure. Graph 800 can be a graph generated by graph construction engine 142. The structure of the graph can be based on the feature data (e.g., feature data similar to that shown in data structure 700 of FIG. 7). Each node (e.g., nodes 810, 820, and 830) can represent a professional that exists in the feature data. Each edge (e.g., edges 815) can represent a similarity between the nodes the edge connects.

Although FIG. 8 shows a visual representation of graph 800 that can include visual elements to represent the nodes, edges, and other information associated with the graph, it is appreciated that this is only one representation of graph 800. Graph 800 could also be represented as a list, raw data, or some other representation of the data structure that defines the graph structure, wherein nodes of the graph could be represented as entries (e.g., within the list, raw data, or data structure) and the edges could be represented as links between the entries (or some other indicator associating multiple entries having similarities). As described herein, a graph (e.g., graph 800) encompasses all of these various representations.

Node 820 can represent a professional that is a positive label in the graph structure. A positive label can include a positive classification of a professional. For example a positive label can be applied to a professional considered to be at the top of his or her profession. Depending on the domain and system used to rank professionals, a positive label can be applied to a professional considered to be a 10 out of 10, an A+, a tier 1 professional, or some other relative classification that indicates a professional at the peak of their field. Similarly Node 830 can represent a professional that is a negative label in the data set. Negative labels can represent those professionals identified at the bottom of their field. Example ratings can include a 0 out of 10, an F, a bottom of tier, or some other relative classification of a professional that indicates a professional at the bottom of their field. In creating graph 800, there is a tendency that nodes clustered around positive or negative labels will exhibit similar characteristics.

Referring back to FIG. 1, graph construction engine 142 can generate graph 800 based on the feature data. Graph 800 can be used to further analyze various interactions among the professionals. Graph construction engine 142 can weight edges 815 based on the similarity between the connected professionals. Graph construction engine 142 can use techniques such as, among others, cosine similarity, Gaussian Kernel Similarity, Euclidian distance similarity, Jaccard similarity, and Manhatten similarity.

In addition to weighting the edges (e.g., edges 815 of graph 800), graph construction engine 142 can determine which edges should be included in the graph. By choosing which features define the similarity of the professionals in the feature data (e.g., feature data in data structure 700) represented as nodes (e.g., nodes 810, 820, and 830), graph construction engine 142 can control the number edges in graph 800. The number of edges can be controlled by the threshold that is used by graph construction engine 142 when constructing the graph. If the graph is constructed using k-nearest neighbors, than each node of graph 800 can be connected to the k nodes that are determined to be closest. In some other embodiments, the edges can be constructed by placing edges between nodes that are within a constant value of each other using a predetermined metric. If there are too many edges, the graph will be too noisy and be more difficult to analyze. If there are too few edges, the connections between nodes will not provide enough information to make accurate comparisons among the professionals represented by the nodes. Moreover, graph construction engine 142 can retain edges associated with feature similarity that is most relevant to classify the professionals represented by the nodes as high or low quality.

Figure 9:
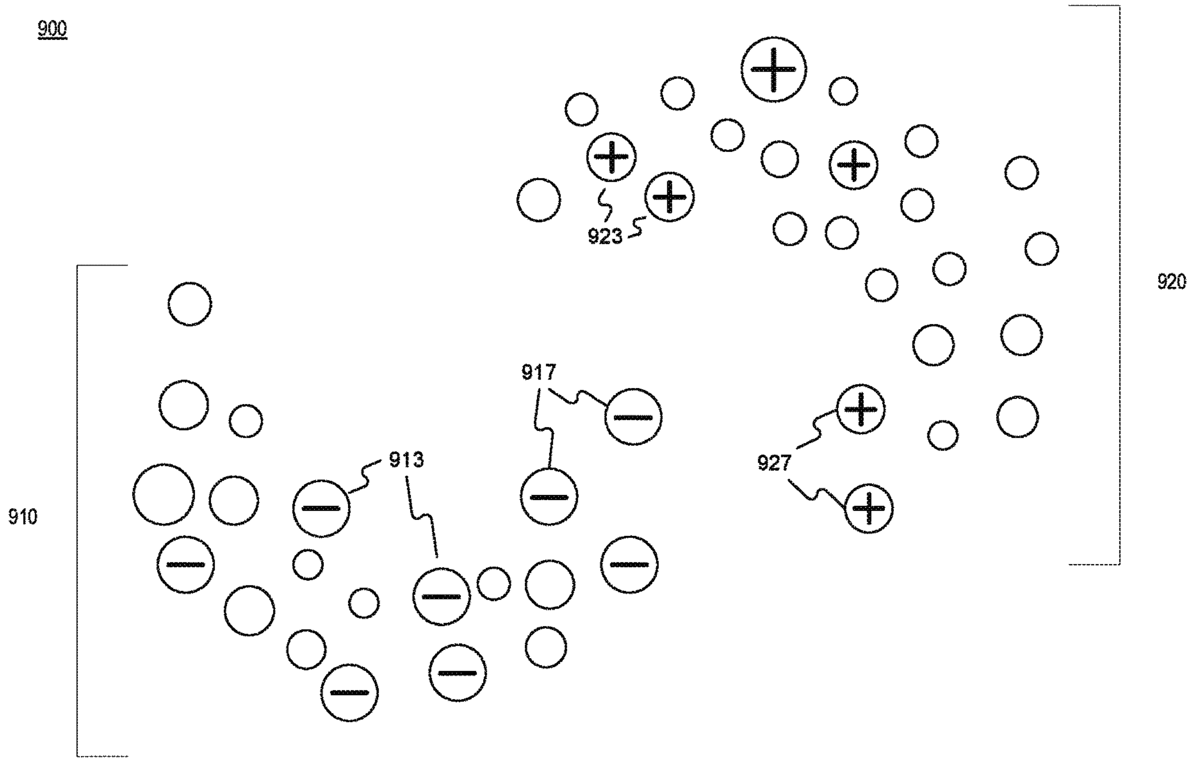
FIG. 9 is an exemplary graph consistent with embodiments of the present disclosure.

As an example of the effect of noise, too many data points can hinder effective analysis. As shown in FIG. 9, clusters of nodes can exist in the data being generated by graph construction engine 142. For example, negative cluster 910 can represent a large cluster of nodes that should all be associated with negative labels and positive cluster 920 can represent a large cluster of nodes that should all be associated with positive labels. Negative labels can be represented by negative nodes 913 in negative cluster 910, and positive labels can be represented by positive nodes 923 in positive cluster 920 respectively. In some embodiments, however, positive nodes that are near negative clusters and negative nodes that are near positive clusters can be mislabeled. For example, positive nodes 927 can, in some cases, be labeled as negative nodes due to their proximity to cluster 910. Similarly, negative nodes 917 can mistakenly be labeled as positive nodes due to their proximity to cluster 920. These labels, which are noise introduced through data processing, can cause portions of negative cluster to be erroneously positive. Similarly, mislabeled positive nodes 927 can have the same effect on cluster 920. Accordingly, over analysis and noise can have detrimental effects. By utilizing methods to choose appropriate edges and labels for the graph creation and through the evaluation process described below noise can be controlled while still providing enough data to have a fully connected graph.

Referring back to FIGS. 1 and 8, different methods exist for choosing appropriate edges and help alleviate both computational complexity and the effects of noise in the system. One approach is to find the k-nearest neighbors to every physician. Various methods for finding the k-nearest neighbors can be used. A brute force approach can be effective but is not always the most efficient approach to choosing relevant edges to include in graph 800. Conversely, other methods of choosing k-nearest neighbors can be more efficient but not as accurate as a brute force approach. In some embodiments, graph construction engine 142 uses a locality sensitive hashing to determine the nearest neighbors to each professional. Graph construction engine 142 can also randomly choose k neighbors from the set of nearest neighbors to each professional. Additional methods of choosing which neighbors for each professional should be represented on the graph exist and can be effective algorithms for placing edges 815 on graph 800.

Whichever algorithm is used, graph construction engine 142 can adjust the number of edges provided by any of the approaches to provide a fully connected graph 800. In determining how many connections are necessary, graph construction engine can utilize the Erdős-Rényi model. This model can be used to calculate the number of nearest neighbors for each professional that need to be placed on graph 800 as edges 815 to ensure with relative certainty that the graph of all of the professionals constructed from the feature data, represented by nodes 810, 820, and 830 in graph 800, is fully connected.

As graph 800 is constructed by graph construction engine 142, graph construction engine can place the appropriate labels, identified by label engine 130, on graph 800. For example, node 820 can represent a professional identified as a positive label by label engine 130 and node 830 can represent a professional identified as a negative label by label engine 130. These labels, combined with the graph generated by graph construction engine 142, can then be used for further analysis of the non-labeled professionals (e.g., professionals represented by nodes 810).

As described above, graph construction engine 142 can utilize a variety of techniques to efficiently and effectively analyze the feature data provided by feature discovery engine 120 and the labels generated by label engine 130. In using these different techniques, system 100 and graph construction engine 142, can drastically reduce the complexity of the computations necessary to generate graph 800. This reduction in computational complexity can provide reductions in necessary CPU, memory, and computing power allowing for more efficient analysis on large data sets.

As shown in FIG. 1, graph construction engine 142 can also output graph 800 and other data to graph visualization engine 135. Graph visualization engine 135 can process the data associated with a graph (e.g., graph 800) and provide a visual representation of the graph. For example, a visual representation of the graph be similar to the representation of graph 800 in FIG. 8 that includes circles to represent nodes (e.g., nodes 810, 820, and 830) and lines to represent edges (e.g., edges 815) connecting the nodes. Other representations can include a chart, a raw data display, or a textual description of the graph. The visual representation of the graph can be provided to display 193. Display 193 can be, for example, display device 224 of device 200, described below in reference to FIG. 2, or display 306 of client device 300 described below in reference to FIG. 3. In some embodiments, both graph visualization engine 135 and display 193 are part of the same device (e.g., device 200 of FIG. 2 or client device 300 of FIG. 3). In these embodiments, graph visualization engine can directly connect to system 100 or can be connected to system 100 over a network or other communication systems. This connection can be provided by, for example, network interface 218 or I/O devices 230 of FIG. 2 and communications subsystem 304, short-range wireless communications 326, and data port 318 of FIG. 3. In other embodiments, system 100 can include graph visualization engine 135, and graph visualization engine 135 can provide a visual representation to display 193 using a network or some other communication link. Moreover, display 193, or components connected to display 193, can accept user input and provide that input to graph visualization engine 135. For example, user input can be captured by I/O devices 230 or network interface 218 of device 200 in FIG. 2 or input devices 308, short-range wireless communications 326, and communications subsystem 304 of client device 300 in FIG. 3.

After graph construction engine 142 generates a graph (e.g., graph 800 of FIG. 8) that represents the feature data (e.g., data structure 700 of FIG. 7) that includes labels identified by label engine 130, label propagation engine 144 can begin analyzing the graph structure by propagating positive and negative labels throughout the nodes of the graph.

Different methods exist for propagating labels through the graph based on the known labels. In some embodiments propagation can be achieved using various graph kernel algorithms and diffusion algorithms. Other graph modeling methods can be used to propagate the labels.

In some embodiments, the label propagation engine 144 treats the positive and negative labels as positive and negative charges on the graph. The positive labels and negative labels (e.g., nodes 820 and 830 of graph 800 in FIG. 8) can represent boundary conditions. Label propagation engine 144 can then use Laplace's equation on the graph to identify the charge potential for each node in the graph based on the boundary conditions. In using this equation on graph 800, label propagation engine 144 can determine the relative rank of the various nodes in the graph based on the initial point charges.

Similarly, in some embodiments, the positive and negative labels can be treated as Coulomb potentials for use with Poisson's equation on the graph. As described above, the resulting potential of the non-labeled nodes (e.g., nodes 810 of graph 800) can be associated with a relative ranking from high quality to low quality based on the effect of the labeled nodes (e.g., nodes 820 or 830). Because each node is mapped to a professional represented in the feature data (e.g., data structure 700 of FIG. 7), the calculated Coulomb potential from label propagation engine 144 can be used to rank the professionals. By using electrostatic equations, label propagation engine 144 can model the effects of the positive and negative labels as they spread to distant portions of the graph in ways that are not apparent through visual inspection, manual inspection, or other analysis.

After analyzing the graph (e.g., graph 800), label propagation engine 144 can provide a ranking of the nodes, and by their representation, the professionals based on the calculated values for each node. This ranking can be provided to graph visualization engine 135 and can also be provided to app engine 170. Similarly to graph visualization engine 135, app engine 170 can provide additional output to display 190. The output can include a visual representation of the updated graph (e.g., graph 800), a chart representing the graph or relative rankings of the nodes, or other textual and/or graphical information representing the relative rankings of the nodes and professionals. Display 190 can be, for example, display device 224 of device 200, described below in reference to FIG. 2, or display 306 of client device 300 described below in reference to FIG. 3. In some embodiments, app engine 170 and display 190 are part of the same device (e.g., device 200 of FIG. 2 or client device 300 of FIG. 3). In these embodiments, graph visualization engine can directly connect to system 100 or can be connected to system 100 over a network or other communication system. This connection can be provided by, for example, network interface 218 or I/O devices 230 of FIG. 2 and communications subsystem 304, short-range wireless communications 326, and data port 318 of FIG. 3. In other embodiments, system 100 can include graph visualization engine 135, and graph visualization engine 135 can provide a visual representation to display 190 using a network or some other communication link. Moreover, display 190, or components connected to display 190, can accept user input and provide that input to app engine 170. For example, user input can be captured by I/O devices 230 or network interface 218 of device 200 in FIG. 2 or input devices 308, short-range wireless communications 326 communications subsystem 304 of client device 300 in FIG. 3.

App engine 170 can be used to provide information about the ranking and classification of professionals based on their relative ranking score by label propagation engine 144. In some embodiments, app engine 170 does not directly display the output of label propagation engine 144, but, rather, is used to generate a graphical user interface capable of interpreting the output and displaying that output for use. In other embodiments, the graphical user interface can display the output of propagation engine 144 directly.

In addition to app engine 170 and graph visualization engine 135, the output of label propagation engine 144 can be provided to evaluation engine 160. Evaluation engine 160 can evaluate the results of label propagation engine 144 to determine the effectiveness of the analysis and determinations made by system 100. Various methods for this analysis exist. In some embodiments, evaluation engine 160 uses a Discounted Cumulative Gain (DCG) algorithm to evaluate the rankings produced by label propagation engine 144.

Additional input sources and training data, such as customer or, in a healthcare context, patient feedback can be used to evaluate the relevance of the produced rankings. In some embodiments, Rank Biased Precision ("RBP") can allow the evaluation of the overall quality of a rank of professionals. RBP can conceptualize a user descending down the ranked list using a behavioral model that is controlled by a persistence parameter. The RBP value can depend on a set of graded relevance judgments, which are numerical scores assigned to a small number of professionals. The higher the value of the graded relevance, the larger the contribution to the utility function. In some embodiments, Monte Carlo simulations can further be used to estimate confidence intervals Evaluation engine 160 can provide information and output to dashboard engine 180. Dashboard engine 180 can format the data and receive input that can be used to configure system 100 and adjust the various components of system 100. Similarly to app engine 170 and graph visualization engine 135, dashboard engine 180 can provide additional output to display 191. The output can include a visual representation of the updated graph (e.g., graph 800), a chart representing the graph or relative rankings of the nodes, or other textual and/or graphical information representing the relative rankings of the nodes and professionals. Display 191 can be, for example, display device 224 of device 200, described below in reference to FIG. 2, or display 306 of client device 300 described below in reference to FIG. 3. In some embodiments, app engine 170 and display 191 are part of the same device (e.g., device 200 of FIG. 2 or client device 300 of FIG. 3). In these embodiments, graph visualization engine can directly connect to system 100 or can be connected to system 100 over a network or other communication system. This connection can be provided by, for example, network interface 218 or I/O devices 230 of FIG. 2 and communications subsystem 304, short-range wireless communications 326, and data port 318 of FIG. 3. In other embodiments, system 100 can include dashboard engine 180, and dashboard engine 180 can provide a visual representation in the form of a graphical user interface to display 191 using a network or some other communication link. Moreover, display 191, can accept user input and provide that input to dashboard engine 180. For example, user input can be captured by I/O devices 230 or network interface 218 of device 200 in FIG. 2 or input devices 308, short-range wireless communications 326 communications subsystem 304 of client device 300 in FIG. 3.

Figure 2:
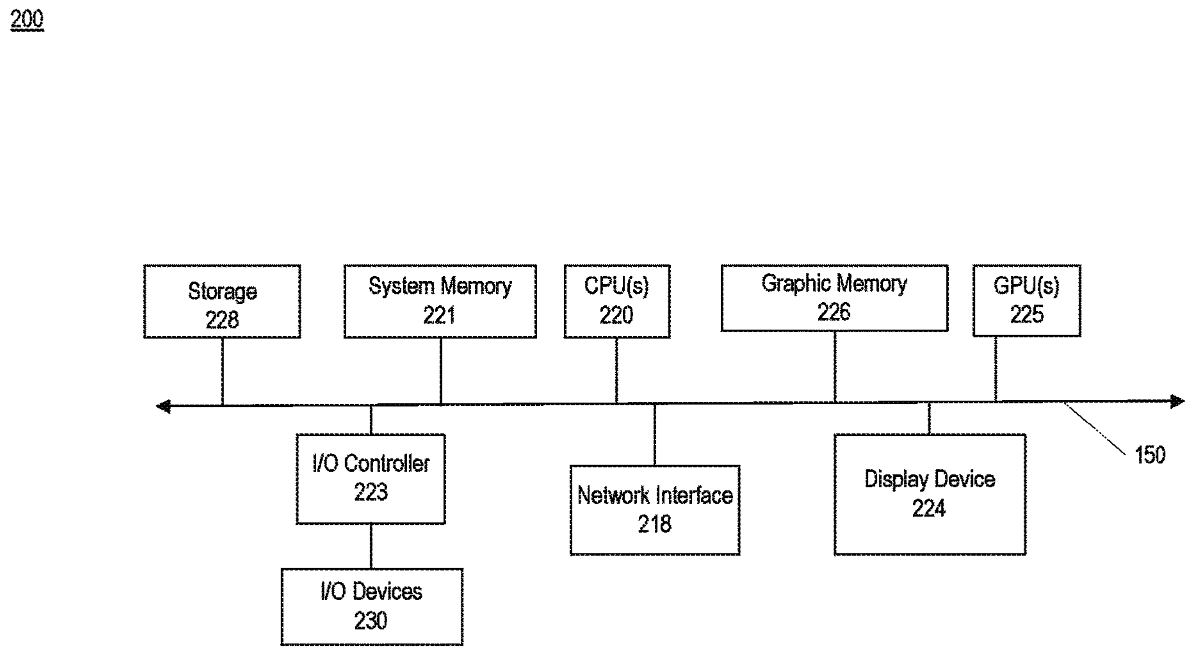
FIG. 2 is a block diagram of an exemplary computing device, consistent with embodiments of the present disclosure.

FIG. 2 is a block diagram of an exemplary computing device 200, consistent with embodiments of the present disclosure. In some embodiments, computing device 200 can be a specialized server providing the functionality described herein. In some embodiments, system 100 is implemented using computing device 200 or multiple computing devices 200 operating in parallel. Further, computing device 200 can be a second device providing the functionality described herein or receiving information from a server to provide at least some of that information for display. Moreover, computing device 200 can be an additional device or devices that store and/or provide data consistent with embodiments of the present disclosure.

Computing device 200 can include one or more central processing units (CPUs) 220 and system memory 221. Computing device 200 can also include one or more graphics processing units (GPUs) 225 and graphic memory 226. CPUs 220 can be single or multiple microprocessors, field-programmable gate arrays, or digital signal processors capable of executing sets of instructions stored in a memory (e.g., system memory 221), a cache, or a register. CPUs 220 can contain one or more registers for storing variable types of data including, inter alia, data, instructions, floating point values, conditional values, memory addresses for locations in memory (e.g., system memory 221 or graphic memory 226), pointers and counters. CPU registers can include special purpose registers used to store data associated with executing instructions such as an instruction pointer, instruction counter, and/or memory stack pointer. System memory 221 can include a tangible and/or non-transitory computer-readable medium, such as a flexible disk, a hard disk, a compact disk read-only memory (CD-ROM), magneto-optical (MO) drive, digital versatile disk random-access memory (DVD-RAM), a solid-state disk (SSD), a flash drive and/or flash memory, processor cache, memory register, or a semiconductor memory. System memory 221 can be one or more memory chips capable of storing data and allowing direct access by CPUs 220. System memory 221 can be any type of random access memory (RAM), or other available memory chip capable of operating as described herein.

CPUs 220 can communicate with system memory 221 via a system interface 250, sometimes referred to as a bus. GPUs 225 can be any type of specialized circuitry that can manipulate and alter memory (e.g., graphic memory 226) to provide and/or accelerate the creation of images. GPUs 225 can store images in a frame buffer for output to a display device such as display device 224. GPUs 225 can have a highly parallel structure optimized for processing large, parallel blocks of graphical data more efficiently than general purpose CPUs 220. Furthermore, the functionality of GPUs 225 can be included in a chipset of a special purpose processing unit or a co-processor.

CPUs 220 can execute programming instructions stored in system memory 221 or other memory, operate on data stored in memory (e.g., system memory 221) and communicate with GPUs 225 through the system interface 250, which bridges communication between the various components of computing device 200. In some embodiments, CPUs 220, GPUs 225, system interface 250, or any combination thereof, are integrated into a single chipset or processing unit. GPUs 225 can execute sets of instructions stored in memory (e.g., system memory 221), to manipulate graphical data stored in system memory 221 or graphic memory 226. For example, CPUs 220 can provide instructions to GPUs 225, and GPUs 225 can process the instructions to render graphics data stored in the graphic memory 226. Graphic memory 226 can be any memory space accessible by GPUs 225, including local memory, system memory, on-chip memories, and hard disk. GPUs 225 can enable displaying of graphical data stored in graphic memory 226 on display device 224.

Computing device 200 can include display device 224 and input/output (I/O) devices 230 (e.g., a keyboard, a mouse, or a pointing device) connected to I/O controller 223. I/O controller 223 can communicate with the other components of computing device 200 via system interface 250. It is appreciated that CPUs 220 can also communicate with system memory 221 and other devices in manners other than through system interface 250, such as through serial communication or direct point-to-point communication. Similarly, GPUs 225 can communicate with graphic memory 226 and other devices in ways other than system interface 250. In addition to receiving input, CPUs 220 can provide output via I/O devices 230 (e.g., through a printer, speakers, or other output devices).

Furthermore, computing device 200 can include a network interface 218 to interface to a LAN, WAN, MAN, or the Internet through a variety of connections including, but not limited to, standard telephone lines, LAN or WAN links (e.g., 802.21, T1, T3, 56 kb, X.25), broadband connections (e.g., ISDN, Frame Relay, ATM), wireless connections, or some combination of any or all of the above. Network interface 218 can comprise a built-in network adapter, network interface card, PCMCIA network card, card bus network adapter, wireless network adapter, USB network adapter, modem or any other device suitable for interfacing computing device 200 to any type of network capable of communication and performing the operations described herein.

Figure 3:
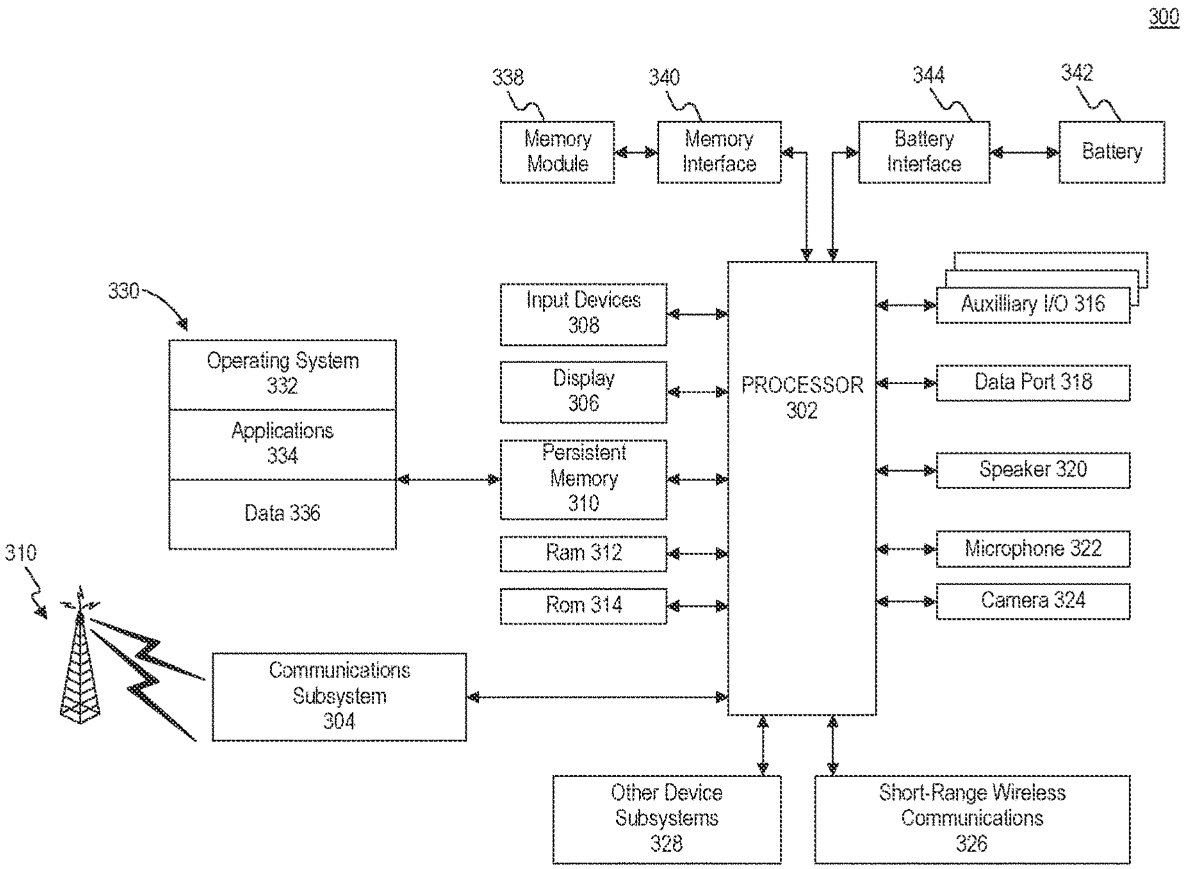
FIG. 3 is a block diagram of an exemplary computing device, consistent with embodiments of the present disclosure.

FIG. 3 is a simplified block diagram illustrating an example electronic device 300. In some embodiments, electronic device 300 can include a communication device having two-way or one-to-many data communication capabilities, audio communication capabilities, and/or video communication capabilities, and the capability to communicate with other computer systems, for example, via the Internet. Depending on the functionality provided by electronic device 300, in various embodiments, electronic device 300 can be a handheld device, a multiple-mode communication device configured for both data and voice communication, a smartphone, a mobile telephone, a laptop, a computer wired to the network, a netbook, a gaming console, a tablet, a smart watch, or a PDA enabled for wireless communication.

Electronic device 300 can include a case (not shown) housing component of electronic device 300. The internal components of electronic device 300 can, for example, be constructed on a printed circuit board (PCB). The description of electronic device 300 herein mentions a number of specific components and subsystems. Although these components and subsystems can be realized as discrete elements, the functions of the components and subsystems can also be realized by integrating, combining, or packaging one or more elements in any suitable fashion.

Electronic device 300 can include a controller comprising at least one processor 302 (such as a microprocessor), which controls the overall operation of electronic device 300. Processor 302 can be one or more microprocessors, field programmable gate arrays (FPGAs), digital signal processors (DSPs), or any combination thereof capable of executing particular sets of instructions. Processor 302 can interact with device subsystems such as a communication subsystem 304 for exchanging radio frequency signals with a wireless network to perform communication functions.

Processor 302 can also interact with additional device subsystems including a communication subsystem 304, a display 306 (e.g., a liquid crystal display (LCD) screen, a touch-screen display, or any other appropriate display), input devices 308 (e.g., a keyboard, a stylus, or control buttons), a persistent memory 310, a random access memory (RAM) 312, a read only memory (ROM) 314, auxiliary input/output (I/O) subsystems 316, a data port 318 (e.g., a conventional serial data port, a Universal Serial Bus (USB) data port, a 30-pin data port, a Lightning data port, or a High-Definition Multimedia Interface (HDMI) data port), a speaker 320, a microphone 322, camera 324, a short-range wireless communications subsystem 326 (which can employ any appropriate wireless (e.g., RF), optical, or other short range communications technology (for example, Bluetooth or NFC)), and other device subsystems generally designated as 328. Some of the subsystems shown in FIG. 3 perform communication-related functions, whereas other subsystems can provide "resident" or on-device functions.

Communication subsystem 304 includes one or more communication systems for communicating with a network to enable communication with social networking services 104A-C and any external devices (e.g., a server, not shown). The particular design of communication subsystem 304 depends on the wireless network in which electronic device 300 is intended to operate. Electronic device 300 can send and receive communication signals over the wireless network after the required network registration or activation procedures have been completed.

In some embodiments, display 306 can be a touch-screen display. The touch-screen display can be constructed using a touch-sensitive input surface, which is coupled to an electronic controller and which overlays the visible element of display 306. The touch-sensitive overlay and the electronic controller provide a touch-sensitive input device and processor 302 interacts with the touch-sensitive overlay via the electronic controller.

Camera 324 can be a CMOS camera, a CCD camera, or any other type of camera capable of capturing and outputting compressed or uncompressed image data such as still images or video image data. In some embodiments electronic device 300 can include more than one camera, allowing the user to switch, during a video conference call, from one camera to another, or to overlay image data captured by one camera on top of image data captured by another camera. Image data output from camera 324 can be stored in, for example, an image buffer, which can be a temporary buffer residing in RAM 312, or a permanent buffer residing in ROM 314 or persistent memory 310. The image buffer can be, for example, a first-in first-out (FIFO) buffer.

Short-range wireless communications subsystem 326 is an additional optional component that provides for communication between electronic device 300 and different systems or devices, which need not necessarily be similar devices. For example, short-range wireless communications subsystem 326 can include an infrared device and associated circuits and components, or a wireless bus protocol compliant communication device such as a Bluetooth® communication module to provide for communication with similarly-enabled systems and devices.

Processor 302 can be one or more processors that operate under stored program control and executes software modules 330 stored in a tangibly-embodied non-transitory computer-readable storage medium such as persistent memory 310, which can be a register memory, a processor cache, a Random Access Memory (RAM), a flexible disk, a hard disk, a CD-ROM (compact disk-read only memory), and MO (magneto-optical), a DVD-ROM (digital versatile disk-read only memory), a DVD RAM (digital versatile disk-random access memory), or other semiconductor memories.

Software modules 330 can also be stored in a computer-readable storage medium such as ROM 314, or any appropriate persistent memory technology, including EEPROM, EAROM, FLASH. These computer-readable storage mediums store computer-readable instructions for execution by processor 302 to perform a variety of functions on electronic device 300. Alternatively, functions and methods can also be implemented in hardware components or combinations of hardware and software such as, for example, ASICs and/or special purpose computers.

Software modules 330 can include operating system software 332, used to control operation of electronic device 300. Additionally, software modules 330 can include software applications 334 for providing additional functionality to electronic device 300. For example, software applications 334 can include applications designed to interface with systems like system 100 above (e.g., software applications 334 can include implementations of app engine 170, dashboard engine 180, and graph visualization engine 135 described above in reference to FIG. 1).

Software applications 334 can also include a range of applications, including, for example, an e-mail messaging application, an address book, a notepad application, an Internet browser application, a voice communication (i.e., telephony or Voice over Internet Protocol (VoIP)) application, a mapping application, a media player application, a health-related application, a benefits-related application, etc. Each of software applications 334 can include layout information defining the placement of particular fields and graphic elements (for example, text fields, input fields, icons, etc.) in the user interface (e.g., user interfaces 300 shown in FIG. 3) according to that corresponding application.

Operating system software 332 can provide a number of application protocol interfaces (APIs) providing an interface for communicating between the various subsystems and services of electronic device 300, and software applications 334. For example, operating system software 332 provides a user interface API to any application that needs to create user interfaces for display on electronic device 300. Accessing the user interface API can provide the application with the functionality to create and manage screen windows and user interface controls, such as text boxes, buttons, and scrollbars; receive mouse and keyboard input; and other functionality intended for display on display 306. Furthermore, a camera service API can allow a video communication application to access camera 324 for purposes of capturing image data (such as an image or video data that can be shared using the social networking services).

In some embodiments, persistent memory 310 stores data 336, including data specific to a user of electronic device 300, such as information of user accounts. Persistent memory 310 can also store data relating to those (e.g., contents, notifications, and messages) obtained from social networking services, data to be shared using the social networking services, or search results. Persistent memory 310 can further store data relating to various applications with preferences of the particular user of, for example, electronic device 300. In some embodiments, persistent memory 310 can store data 336 linking a user's data with a particular field of data in an application, such as for automatically entering a user's name into a username textbox on an application executing on electronic device 300. Furthermore, in various embodiments, data 336 can also include service data comprising information required by electronic device 300 to establish and maintain communication with a network.

In some embodiments, auxiliary input/output (I/O) subsystems 316 comprise an external communication link or interface, for example, an Ethernet connection. In some embodiments, auxiliary I/O subsystems 316 can further comprise one or more input devices, including a pointing or navigational tool such as a stylus, a clickable trackball or scroll wheel or thumbwheel, or a human finger; and one or more output devices, including a mechanical transducer such as a vibrator for providing vibratory notifications in response to various events on electronic device 300 (for example, receipt of a notification or a message or an incoming phone call), or for other purposes such as haptic feedback (touch feedback); or any combination thereof.

In some embodiments, electronic device 300 can also include one or more removable memory modules 338 (e.g., FLASH memory) and a memory interface 340. Removable memory module 338 can store information used to identify or authenticate a user or the user's account to a wireless network. For example, in conjunction with certain types of wireless networks, including GSM and successor networks, removable memory module 338 is referred to as a Subscriber Identity Module (SIM). Memory module 338 can be inserted in or coupled to memory module interface 340 of electronic device 300 in order to operate in conjunction with the wireless network.

Electronic device 300 can also include a battery 342, which furnishes energy for operating electronic device 300. Battery 342 can be coupled to the electrical circuitry of electronic device 300 through a battery interface 344, which can manage such functions as charging battery 342 from an external power source (not shown) and the distribution of energy to various loads within or coupled to electronic device 300.

A set of applications that control basic device operations, including data and possibly voice communication applications, can be installed on electronic device 300 during or after manufacture. Additional applications or upgrades to operating system software 332 or software applications 334 can also be loaded onto electronic device 300 through a wireless network, auxiliary I/O subsystem 316, data port 318, short-range wireless communication subsystem 326, or other suitable subsystem such as 328. The downloaded programs or code modules can be permanently installed, for example, written into the persistent memory 310, or written into and executed from RAM 312 for execution by processor 302 at runtime.

Electronic device 300 can provide three principal modes of communication: a data communication mode, a voice communication mode, and a video communication mode. In the data communication mode, a received data signal such as a text message, an e-mail message, Web page download, VoIP data, or an image file are processed by communication subsystem 304 and input to processor 302 for further processing. For example, a downloaded Web page can be further processed by a browser application, or data obtained from social networking services can be processed by a unified social networking application and output to display 306. A user of electronic device 300 can also compose data items, such as contents for sharing using social networking services, e-mail messages, for example, using the input devices, such as auxiliary I/O subsystem 316, in conjunction with display 306. These composed items can be transmitted through communication subsystem 304 over a wireless network. In the voice communication mode, electronic device 300 provides telephony functions and operates as a typical cellular phone. In the video communication mode, electronic device 300 provides video telephony functions and operates as a video teleconference terminal. In the video communication mode, electronic device 300 utilizes one or more cameras (such as camera 324) to capture video for the video teleconference.

Figure 10:
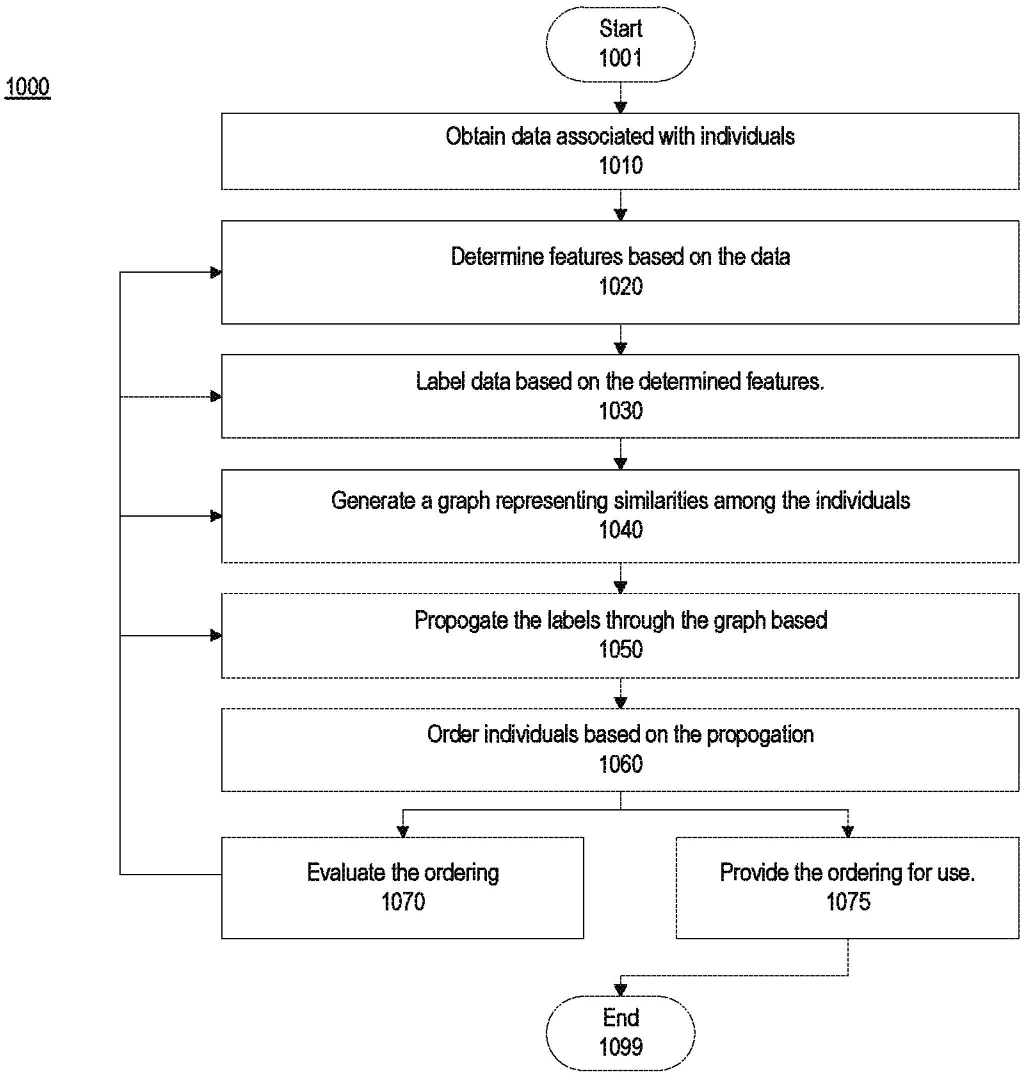
FIG. 10 is a flowchart of an exemplary method for data driven analysis, modeling, and semi-supervised machine learning, consistent with embodiments of the present disclosure.

FIG. 10 is a flowchart of an exemplary method 1000 for data driven analysis, modeling, and semi-supervised machine learning for qualitative and quantitative determinations, consistent with embodiments of the present disclosure. It will be readily appreciated that the illustrated procedure can be altered to delete steps or further include additional steps. It is appreciated that one or more computing devices (such as computing device of FIG. 2) can perform the exemplary method and that the functionality described herein can be incorporated as hardware, software stored in the one or more computing devices, or any combination thereof. Moreover, the illustrated procedure can be applied to many different domains and descriptions related to a healthcare context are not intended to limit the disclosure to only that domain. After initial step 1001, the system (e.g., system 100 from FIG. 1) can obtain (step 1010) data associated with individuals (e.g., professionals or, in a healthcare context, physicians stored in data structure 400 of FIG. 4). Obtaining the data can include, as described in relation to FIG. 1 extracting (e.g., using data extractor 111) the data from multiple data sources (e.g., data sources 101-104), transforming the data (e.g., using data transformer 112), and loading the data (e.g., using data loader 113) into a storage location (e.g., data storage 115) for additional analysis. Through this process, the system can prepare data from a variety of sources into a normalized and consistent representation ready for further processing.

The system can determine (step 1020) features (e.g., using feature discovery engine 120) based on the data stored in the storage location (e.g., data storage 115). This data can include, among other things, physician data (e.g., data structure 400 of FIG. 4), claims data (e.g., data structure 500 of FIG. 5), and prescription data (e.g., data structure 600 of FIG. 6). Based on this data, the system can generate features associated with physicians (e.g., data structure 700 of FIG. 7).

The system can further label (step 1030) the feature data by determining (e.g., using label engine 130) which physicians are of higher and lower quality. The identification of high and low quality physicians can be based on the feature data. Certain features can be determined to be signals of good and bad physicians. For example, good physicians can be identified as those who generate a large amount of RVUs when compared to similar physicians in the same specialty. Additional positive signals can include features related to educational background, professional recognition, professional experience, or other identified signals. Examples of signals for negative labels include, among others, sanctions, reprimands, lack of scholarship, and patient complaints. After an initial set of physicians are labeled using these various signals, the nearest neighbors to labeled physicians can be calculated to expand the number of labeled physicians.

After generating the labels, the system can generate (step 1040) a graph (e.g., using graph construction engine 142) representing similarities among the physicians. The graph can include nodes representing each physicians and edges connecting the nodes that are similar. The number of edges chosen can be based on various formulas including, among others, choosing k nearest neighbors, cosine similarity, Gaussian Kernel Similarity, or Euclidian distance similarity among the physicians. Furthermore, the system can use methods such as the Erdős-Rényi model to choose enough edges to provide a fully connected graph while at the same time reducing the computational complexity and noise to manageable levels. After generating the graph, the system can further include the positive and negative labels that were determined on the nodes of the graph representing those identified physicians.

After generating the graph, the system can propagate (step 1050) the labels (e.g., using label propagation engine 144) to the unlabeled nodes of the graph. The system can treat the positive and negative labels as point charges in an electrostatic system. The system can then calculate the electrical potential of the nodes using equations for analyzing electrical systems such as Laplace's equation or Poisson's equation. The electrical potential for each node can be converted into a relative ranking of physicians based on the calculated electrical potential of each node in the graph.

After propagating the labels, the system can order (step 1060) the physicians based on the propagation of the labels. The relative ordering can be based on the relative amount of the point charges calculated for each of the nodes. The system can evaluate (step 1070) the ordering by determining the relevance of the ordered results. The system can use process such as DCG to determine the efficacy of the generated ordering. The result of the evaluations can be used to adjust the operation of the other parts of the system (e.g., feature discovery engine 120, label engine 130, graph construction engine 142, and label propagation engine 144).

Alternatively the system can provide (step 1075) the ordering for use (e.g., through app engine 170 or dashboard engine 180) by various users of the system. These users can include individuals using the output to find physicians or individuals using the system provide recommendations about physicians. Other uses for this information are possible, and different outputs can be generated by adjusting the specific features, labels, and propagation methods used throughout the system.

Although the system is described in terms of a healthcare context, the system can be used for many different domains. The features used and data that is input can be based on the nuances as specifics of the domain being analyzed.

In the foregoing specification, embodiments have been described with reference to numerous specific details that can vary from implementation to implementation. Certain adaptations and modifications of the described embodiments can be made. Other embodiments can be apparent to those skilled in the art from consideration of the specification and practice of the invention disclosed herein. It is intended that the specification and examples be considered as exemplary only. It is also intended that the sequence of steps shown in figures are only for illustrative purposes and are not intended to be limited to any particular sequence of steps. As such, those skilled in the art can appreciate that these steps can be performed in a different order while implementing the same method.

What is claimed is:

1. A non-transitory computer readable storage medium storing instructions that are executable by a first computing device that includes one or more processors to cause the first computing device to perform a method comprising:

obtaining, from one or more data sources, one or more data sets associated with a plurality of professionals;

determining features associated with the plurality of professionals;

determining similarities among the plurality of professionals based on the determined features;

generating data representing a connected graph based on the determined similarities and the determined features, wherein nodes of the graph are associated with the plurality of professionals;

determining a first set of labels for a first subset of the plurality of professionals;

annotating a first subset of nodes of the graph with the first set of labels;

annotating a second subset of nodes of the graph with a second set of labels by propagating the first set of labels to the second subset of nodes of the graph;

ranking the plurality of professionals based on the first set of labels and the second set of labels; and providing output associated with the ranking.

2. The non-transitory computer readable storage medium of claim 1, wherein generating data representing a connected graph utilizes a random graph model to select a subset of nodes to connect using edges on the graph.

3. The non-transitory computer readable storage medium of claim 1, wherein edges of the graph are weighted and the weight of the edges are based on the determined similarities.

4. The non-transitory computer readable storage medium of claim 1, wherein the set of labels includes at least one of positive labels and negative labels.

5. The non-transitory computer readable storage medium of claim 1, wherein propagating the first set of labels to the second subset of nodes of the graph further comprises:

identifying a second subset of the plurality of professionals that are similar to at least one professional of the first subset of the plurality of professionals based on determined similarities;

determining the second subset of labels for the second subset of the plurality of professionals based on determined features among the first subset of the plurality of professionals and the second subset of the plurality of professionals;

annotating the second subset of nodes of the graph using the second subset of labels.

6. The non-transitory computer readable storage medium of claim 1, wherein the graph includes weighted nodes and unweighted nodes, wherein the weighted nodes are based on the first set of labels.

7. The non-transitory computer readable storage medium of claim 6, wherein propagating the first set of labels to the second subset of nodes of the graph further comprises:

weighting the unweighted nodes of the graph wherein the weights are based on an influence exerted by the weighted nodes on the unweighted nodes.

8. The non-transitory computer readable storage medium of claim 7, wherein the influence of the weighted nodes on the unweighted nodes is determined using Poisson's equation, Laplace's equation, a Laplacian exponential diffusion kernel, a regularized Laplacian kernel, or a Von Neumann diffusion kernel.

9. The non-transitory computer readable storage medium of claim 1, wherein providing the output further comprises providing the data representing the graph and the output associated with the ranking for processing by a client device.

10. The non-transitory computer readable storage medium of claim 1, wherein providing output further comprises providing the output for display on a graphical user interface.

11. A data-driven analysis system comprising:

one or more memory devices storing processor executable instructions; and one or more processors configured to execute the instructions to cause the data-driven analysis system to perform:

obtaining, from one or more data sources, one or more data sets associated with a plurality of professionals;

determining features associated with the plurality of professionals;

determining similarities among the plurality of professionals based on the determined features;

generating data representing a connected graph based on the determined similarities and the determined features, wherein nodes of the graph are associated with the plurality of professionals;

determining a first set of labels for a first subset of the plurality of professionals;

annotating a first subset of nodes of the graph with the first set of labels;

annotating a second subset of nodes of the graph with a second set of labels by propagating the first set of labels to the second subset of nodes of the graph;

ranking the first set of plurality of professionals based on the first set of labels and the second set of labels; and providing output associated with the ranking.

12. The data-driven analysis system of claim 11, wherein edges of the graph are weighted and the weight of the edges are based on the determined similarities.

13. The data-driven analysis system of claim 11, wherein propagating the first set of labels to the second subset of nodes of the graph further comprises:

identifying a second subset of the plurality of professionals that are similar to at least one professional of the first subset of the plurality of professionals based on determined similarities;

determining a second subset of labels for the second subset of the plurality of professionals, wherein the second subset of labels are based on determined feature among the first subset of the plurality of professionals and the second subset of the plurality of professionals;

annotating the second subset of nodes of the graph using the second subset of labels.

14. The data-driven analysis system of claim 11, wherein the graph includes weighted nodes and unweighted nodes, wherein the weighted nodes are based on the first set of labels.

15. The data-driven analysis system of claim 11, wherein propagating the first set of labels to the second subset of nodes of the graph further comprises:

weighting the unweighted nodes of the graph wherein the weights are based on an influence exerted by the weighted nodes on the unweighted nodes.

16. The data-driven analysis system of claim 11, wherein providing the output further comprises providing the data representing the graph and the output associated with the ranking for processing by a client device.

17. A method performed by one or more processors and comprising:

obtaining, from one or more data sources, one or more data sets associated with a plurality of professionals;

determining features associated with the plurality of professionals;

determining similarities among the plurality of professionals based on the determined features;

generating data representing a connected graph based on the determined similarities and the determined features, wherein nodes of the graph are associated with the plurality of professionals;

determining a first set of labels for a first subset of the plurality of professionals;

annotating a first subset of nodes of the graph with the first set of labels;

annotating a second subset of nodes of the graph with a second set of labels by propagating the first set of labels to the second subset of nodes of the graph;

ranking the first set of plurality of professionals based on the first set of labels and the second set of labels; and providing output associated with the ranking.

18. The method of claim 17, wherein the set of labels includes at least one of positive labels and negative labels.

19. The method of claim 18, wherein propagating the first set of labels to the second subset of nodes of the graph further comprises;

identifying a second subset of the plurality of professionals that are similar to at least one professional of the first subset of the plurality of professionals based on determined similarities;

determining a second subset of labels for the second subset of the plurality of professionals, wherein the second subset of labels are based on determined features among the first subset of the plurality of professionals and the second subset of the plurality of professionals;

annotating the second-subset of nodes of the graph using the second subset of labels.

20. The method of claim 19, wherein providing output further comprises providing the output for display on a graphical user interface.

* * * * *